United States Patent [19]

Whitehouse et al.

[11] Patent Number: 5,112,575
[45] Date of Patent: May 12, 1992

[54] POLYNUCLEOTIDE SYNTHESIZER

[75] Inventors: Craig M. Whitehouse, Branford; Glenn P. Whitehouse, Wallingford; Debra A. Sesholtz, West Haven, all of Conn; David Norman, Rochester, N.Y.

[73] Assignee: Eastman Kodak Company, Rochester, N.Y.

[21] Appl. No.: 657,871

[22] Filed: Feb. 14, 1991

Related U.S. Application Data

[62] Division of Ser. No. 285,277, Dec. 16, 1988, abandoned.

[51] Int. Cl.$^5$ .................. G05D 7/00; C12M 1/40; C12M 1/36
[52] U.S. Cl. .................. 422/116; 422/81; 422/110; 422/112; 422/114; 422/115; 435/288; 435/289; 935/88
[58] Field of Search .............. 422/110, 111, 112, 114, 422/115, 116, 81, 131, 134, 211; 435/287, 288, 289; 935/88; 436/89, 90, 161

[56] References Cited

U.S. PATENT DOCUMENTS

| | | | |
|---|---|---|---|
| 3,531,258 | 9/1970 | Merrifield et al. | 935/88 |
| 3,557,077 | 1/1971 | Brunfeldt | 935/88 |
| 3,647,390 | 3/1972 | Kubodera et al. | 935/88 |
| 4,353,989 | 10/1982 | Bender | 935/88 |
| 4,399,105 | 8/1983 | Tilgner | 422/112 |
| 4,500,707 | 2/1985 | Caruthers et al. | 536/27 |
| 4,517,338 | 5/1985 | Urdea et al. | 435/287 |
| 4,529,573 | 7/1985 | Varady | 422/112 |
| 4,598,049 | 7/1986 | Zelinka et al. | 935/88 |
| 4,701,304 | 10/1987 | Horn et al. | 935/88 |
| 4,746,490 | 5/1988 | Saneii | 435/289 |
| 4,800,166 | 1/1989 | Horn et al. | 436/89 |

FOREIGN PATENT DOCUMENTS 62-61628   3/1987   Japan .................. 422/112

OTHER PUBLICATIONS

"Synthesis of Deoxyoligonucleotides on a Polymer Support", Matteucci and Caruthers, *J. Am. Chem. Soc.*, vol. 103, p. 185.
"Automate Your DNA Synthesis" by Cruachem, 1986.
"Cruachem manual DNA synthesis".

*Primary Examiner*—Robert J. Warden
*Assistant Examiner*—T. A. Trembley
*Attorney, Agent, or Firm*—Arthur H. Rosenstein; Dana M. Schmidt; Bernard J. Graves, Jr.

[57] ABSTRACT

A polynucleotide synthesizer comprises a supply mechanism for supplying a) liquid reactants for synthesizing peptides or polynucleotides, b) liquid reagents that assist in the synthesis, and c) a wash liquid; a reactor column; a connecting device for fluidly connecting the supply mechanism with the column; apparatus for positively displacing with gas pressure, liquid reactants and reagents, and wash liquid from the supply mechanism into the connecting device; and a controller connected to the column for allowing liquid to flow under the force of the gas pressure and at a controlled rate, into a temporary storage chamber and for thereafter emptying the chamber. The synthesizer is improved in one aspect in that the controller is fluidly positioned only downstream of the reactor column, and the synthesizer further includes valving preventing flow from the controller back to the column, whereby the column is precluded from contamination by reactants or reagents in the controller, and the controller needs no cleaning to prevent it from contaminating the column.

In another aspect the synthesizer further includes a parallel manifold having i) sufficient inlet means to receive either each of the liquid reactants or each of the liquid reagents, ii) a common inlet to receive the wash liquid, and iii) an outlet connected to the connecting device to supply reactant or reagent to the column or to the controller, each of the inlet means including a pair of tandem two-way valves, both of the valves of the pair having a common outlet that feeds into the manifold outlet.

6 Claims, 7 Drawing Sheets

POLYNUCLEOTIDE SYNTHESIZER

This is a division of application Ser. No. 285,277, filed Dec. 16, 1988, now abandoned.

FIELD OF THE INVENTION

This invention relates to an improved apparatus and a method used to synthesize polynucleotides or peptides, preferably in an automated manner.

BACKGROUND OF THE INVENTION

Peptide synthesizers and polynucleotide synthesizers have a source of building blocks, which are, respectively, amino acids and nucleotide bases, that are sequentially supplied to a reactor column where they are chemically reacted to form a peptide or an oligonucleotide. Such a reaction requires carefully controlled conditions in which the presence of an incorrect amino acid (or nucleotide base, respectively), leads to the synthesis of the wrong peptide or an incorrect oligonucleotide. As a result, each stepwise addition is followed by a washing of appropriate flow lines. Although the washing delays the process, the delay is minimized by minimizing the volume of the flow lines involved.

A further aspect of the problem is the method in which the amino acids for the peptide, or nucleotide bases for the oligonucleotide, are supplied from their containers. Positive gas displacement is preferred, inasmuch as any system that attempts to "pull" them out using a vacuum, runs the risk of generating bubbles in the liquid, since the liquid amino acids or nucleotides are not degassed prior to use. However, such positive gas displacement systems in turn render downstream control of the displaced liquid difficult.

DNA synthesizers have been constructed to overcome such a control problem and retain the use of gas displacement of the bases. To allow the bases to flow into the system, including a reactor column, at a controlled rate and volume, a syringe controlling means, also called a controller, has been positioned between the reactant (hereinafter, a "base") outlet line, fed from an 8-port rotary valve, and the reactor column. When the syringe piston is withdrawn by a motor to create a storage chamber, the positive gas pressure on the supply bottles causes one or more bases to feed into the syringe. Thereafter, the syringe piston is reversed and the bases are injected into the reactor column. An example of such a conventional synthesizer is the Autoinject module of the Cruachem DNA synthesizer.

A problem with such an instrument is that the syringe becomes "contaminated" with the bases that are to be delivered to the reactor column, due to its upstream location. Such a condition requires that the syringe be thoroughly cleaned (with acetonitrile) prior to the drawing of the next base in the sequence, since the presence of the wrong base will ruin the DNA sequence. Because of the relatively large volume of the syringe, such cleaning is time-consuming and difficult. Yet, if cleaning is minimized, contamination will occur.

Yet another problem with such instruments is that the syringe controller is not in a position to control the feed of the reagents, such as iodine and the like, needed in the synthesis, since the reagents are fed into the reactor via a line separate from the line supplying the bases.

Still another problem with such a synthesizer has been the use of an 8-port rotary valve to collect the bases sequentially. As the valve wears, it leaks, and the base sequence is no longer free of contamination from other bases. To deal with this problem, parallel manifolds have been suggested as in U.S. Pat. No. 4,598,049. However, the manifolds taught therein do not provide for separate washing of each base inlet in sequence, so that there is the chance that one or more base inlets will be inadequately washed, and contamination will occur.

Thus, prior to this invention there has been a need for a DNA synthesizer that is free of these problems.

SUMMARY OF THE INVENTION

This invention provides a solution to the contamination and/or time delay problems noted above.

More specifically, in accord with one aspect of the invention, there is provided a synthesizer apparatus for synthesizing peptides or polynucleotides, the apparatus including supply means for supplying a) liquid reactants for synthesizing the peptides or polynucleotides, b) liquid reagents that assist in the synthesis, and c) a wash liquid; a reactor column; means for fluidly connecting the supply means with the column; and means for positively displacing with gas pressure, liquid reactants and reagents, and wash liquid from the supply means into the connecting means; and controlling means connected to the column for allowing liquid to flow under the force of the gas pressure and at a controlled rate, into a temporary storage chamber and for thereafter emptying the chamber. The apparatus is improved in that the controlling means is a positive displacement controlling means and is fluidly positioned only downstream of the reactor column, and further the synthesizer includes means for preventing flow from the chamber back to the column, whereby the column is precluded from contamination by reactants or reagents in the controlling means, and the controlling means needs no cleaning to prevent it from contaminating the column.

In accord with another aspect of the invention, there is provided a synthesizer apparatus for synthesizing peptides or polynucleotides, the apparatus including supply means for supplying a) liquid reactants for synthesizing the peptides or polynucleotides, b) liquid reagents that assist in the synthesis, and c) a wash liquid; a reactor column; means for fluidly connecting the supply means with the column; means for positively displacing with gas pressure, liquid reactants and reagents, and wash liquid from the supply means into the connecting means; and controlling means connected to the column for allowing liquid to flow under the force of the gas pressure and at a controlled rate, into a temporary storage chamber and for thereafter emptying the chamber. This apparatus is improved in that the apparatus further includes a parallel manifold having i) sufficient inlet means to receive either each of the liquid reactants or each of the liquid reagents, ii) a common inlet to receive the wash liquid, and iii) an outlet connected to the connecting means to supply reactant or reagent to the column or the controlling means, each of the inlet means including a pair of tandem two-way valves, both of the valves of the pair having a common outlet that feeds into the manifold outlet, one of each pair of the tandem valves being connected to the common inlet for the wash liquid and the other of the valves being connected to the inlet means for one of the liquid reactants or one of the liquid reagents, and means for selectively opening only one of the pairs of valves at a time to a source of wash liquid, in a predetermined sequence, whereby an adequate source of wash liquid can be provided for each of the valve pairs of the parallel manifold.

In accord with yet another aspect of the invention, there is provided a method for drawing reactants and reagents under gas pressure into a reactor column to synthesize a peptide or an polynucleotide, using a liquid controlling means fluidly connected to the column. The method comprises the steps of
  a) drawing under the gas pressure a reactant or reagent from a source of supply first into an outlet common with all reactants or reagents, then into the column, and then into the controlling means,
  b) drawing under the gas pressure a wash liquid through the common outlet, then into the column and then into the controlling means,
  c) and ejecting all liquid out of the controlling means into either a collection container or a waste disposal without passage through the column.

Thus, it is an advantageous feature of the invention that a synthesizer is provided with a positive displacement fluid controlling means, which gives rigid liquid advancement within the synthesizer, that need not be thoroughly washed between base introduction, and still will not contaminate the material that is formed.

It is a related advantageous feature of the invention that such a synthesizer is provided that allows one liquid controlling means to control flow advancement of all the liquids used in the synthesis.

Yet another advantageous feature of the invention is that such a synthesizer is provided that minimizes the chance of contamination occurring in a parallel manifold for supplying reactants or reagents to a reaction column, by providing for the individual washing of each reactant or reagent inlet line.

Yet another advantageous feature of the invention is the use of valves that eliminate pressure spikes in the downstream fluid lines.

Other advantageous features will become apparent upon reference to the following Description of the Preferred Embodiments, when read in light of the attached drawings.

BRIEF DESCRIPTION OF THE DRAWINGS

FIG. 2(A and B) is a schematic illustration of a DNA synthesizer constructed in accordance with the invention;

FIG. 6(A and B) is a schematic illustration of an alternative embodiment for the manifold connected to the reagents, wherein the manifold is a parallel manifold rather than series manifold.

DESCRIPTION OF THE PREFERRED EMBODIMENTS

The invention is described hereinafter with respect to the preferred embodiments of apparatus used for DNA synthesizing. In addition, the invention is applicable to apparatus for synthesizing any polynucleotide sequence, be it DNA or RNA, and to the synthesis of peptides using amino acids. In the case of peptides, instead of using the four nucleotide bases as hereinafter enumerated, the apparatus has as its reactants, some or all of the twenty amino acids used to synthesize peptides, and a different set of reagents and reaction sequences.

Figure 1:
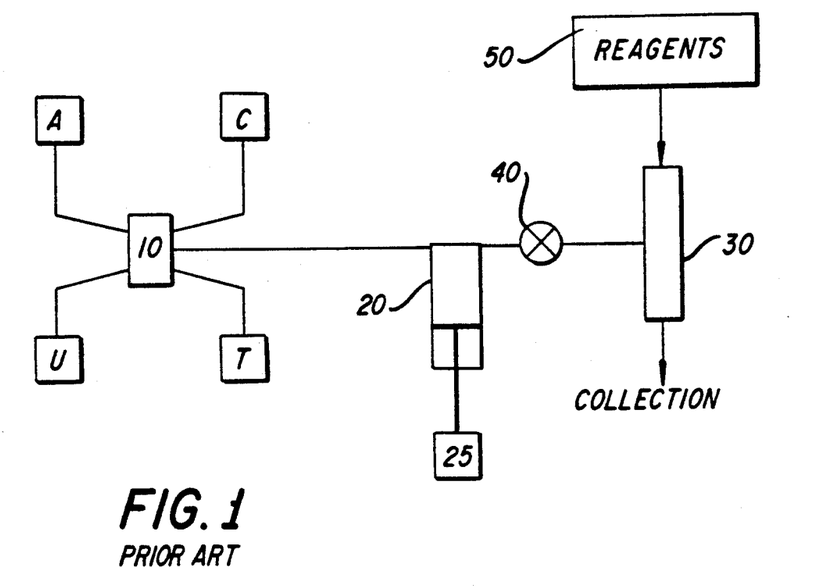
FIG. 1 is a schematic illustration of a DNA synthesizer constructed in accordance with the prior art.

A conventional DNA synthesizer apparatus is illustrated in FIG. 1. In such a device, reactant supply means 10 supplies the four bases A, C, G and T in a particular sequence to a reaction column 30 via a controlling means 20 and two-way valve 40. Preferably, supply means 10 is an 8-port rotary valve and controlling means 20 is a syringe operated by motor 25 and suitable electronic controls, not shown. The capping reagents, along with iodine for oxidation and dichloracetic acid for detritylation, required by the conventional cyanoethylphosphoramidite reaction chemistry, are added separately from supply means 50, and not under the control of controlling means 20. Such an apparatus is provided by the Cruachem DNA Synthesizer noted above, and encounters the disadvantages noted above.

In accord with the invention, the DNA synthesizer 60 preferably comprises, FIG. 2A, supply manifold 70 supplying reactants A, C, G, T, X and Y from bottles 72, 74, 76, 78, 79 and 80, as well as, a tetrazole activator, hereinafter simply "ACT", from bottle 82; supply manifold 90 supplying reagents from bottles 92, 94, 96, 98 and 100, reaction column 110, gas supply manifold 62 for supplying gas pressure to displace liquids from their bottles through the supply manifolds under constant pressure, and positive displacement controlling means 150 for drawing liquid under the force of the gas pressure in response to the actuation of controlling means 150.

Positive displacement controlling means 150 comprises a piston cylinder 158 and a piston 160, and causes positive displacement of liquid due to its downstream location relative to column 110 and to the positive gas pressure applied on the system. That is, as the piston 160 is withdrawn, it allows liquid to flow due to the aforementioned positive pressure. This creates a temporary storage chamber within chamber 158. At the same time, pressures within all the feed lines, such as lines 85 and 114 (referred to hereinafter), remain above atmospheric pressure, as the movement of piston 160 proceeds at a rate that is less than the maximum flow achievable for the pressure of the feed lines in this configuration. As a result, the flow through the entire system is essentially rigid, providing precise flow through any single fluid path.

Any particular synthesis chemistry is usable with this invention, the reagents being selected, of course, to fit the desired scheme. Preferred is the conventional beta cyanoethylphosphoramidite reaction, which uses, for example, iodine for base oxidation and dichloroacetic acid for detritylation. Further detail of the phosphoramidite reaction scheme can be found in Giles and Morrison, "An Economical System for Automated DNA Synthesis", ABL, Vol. 5, p. 16-25 (March/April 1987).

In such a reaction, reactants A, C, G, T and X and Y stand for the following bases: A is adenine, C is cytosine, T is thymine, G is guanine, and X and Y are variables which for example can be U for uracil usually used only in RNA, a mixture of bases, or a modified version of any of the bases. Because the chemistry of such a reaction is well-known, hereinafter details will be directed to the apparatus only.

Gas manifold 62 supplies a non-reactive gas such as helium, argon or nitrogen gas, from an external source 64, through a drier 65 and a pressure regulator valve 66 that maintains the pressure between 0 and 207 kilopascals. Within manifold 62 the incoming line is split into two lines 67 and 68. Lines 67 and 68 are used to pressurize the contents of bottles 72, 74, 76, 78-80 and 92, 94, 96, 98 and 100, respectively, so that when liquid valves are opened downstream, the liquid will exit from the bottles under the influence of the pressure and the appropriate action of controlling means 150. Return lines 69 and 69' vent the gas pressure back through manifold 62 and then to waste. The gas feed line 67 associated with vent line 69 and feed line 68 associated with vent line 69' pressurize their respective manifolds independently, allowing one of two manifolds 70 and 90 to be vented for a bottle change without disturbing the other. The flow in lines 67, 68, 69, and 69' is controlled via conventional valves 17-19, as will be readily apparent.

Turning now to manifolds 70 and 90, each of these is connected to supply bottles via valves, as follows:

For the base manifold 70, preferably each base port thereof has a pair of independently actuated tandem, two-way valves 84. For the reagent manifold 90, each port has a three-way valve 102, except that valve 103 for the $CH_3CN$ can be a two-way valve. These valves utilize non-reactive material such as Teflon TM. For example, valves 84 can be "SV-24" TM valves manufactured by Valcor Scientific, and valves 102 can be "Valcor Series 20" TM valves manufactured also by Valcor Scientific.

Figure 2A:
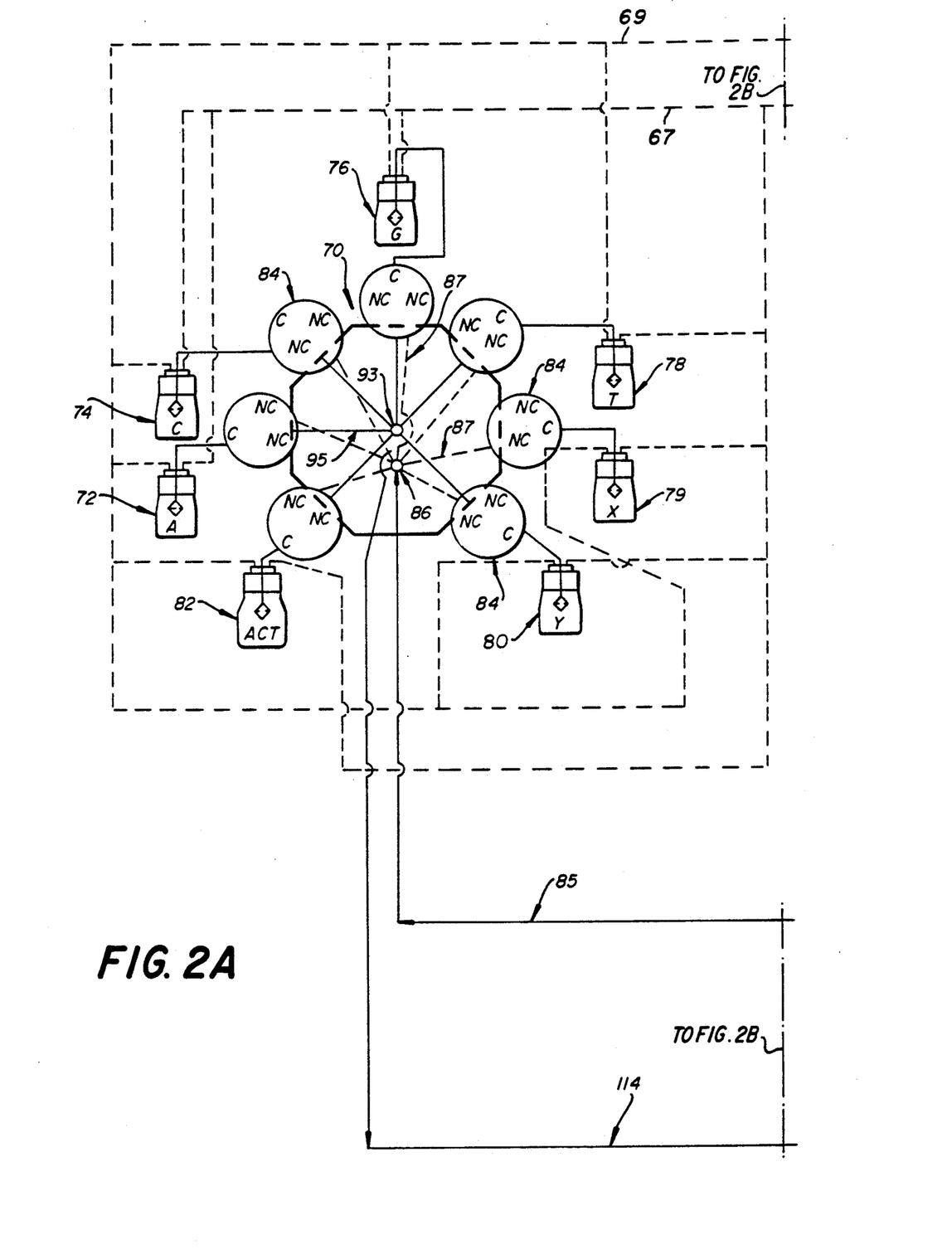
Figure 2B:
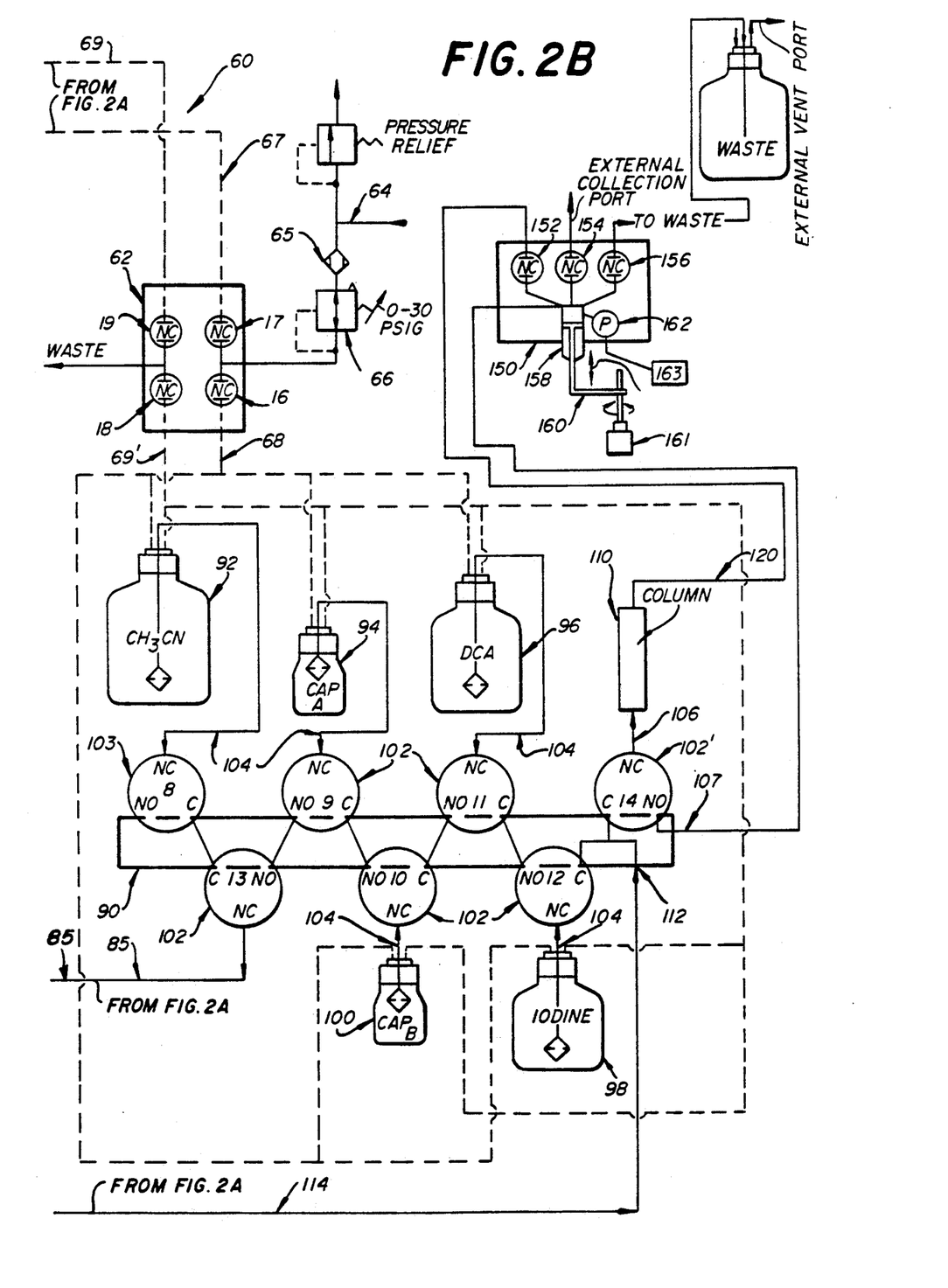
Figures 3, 4:
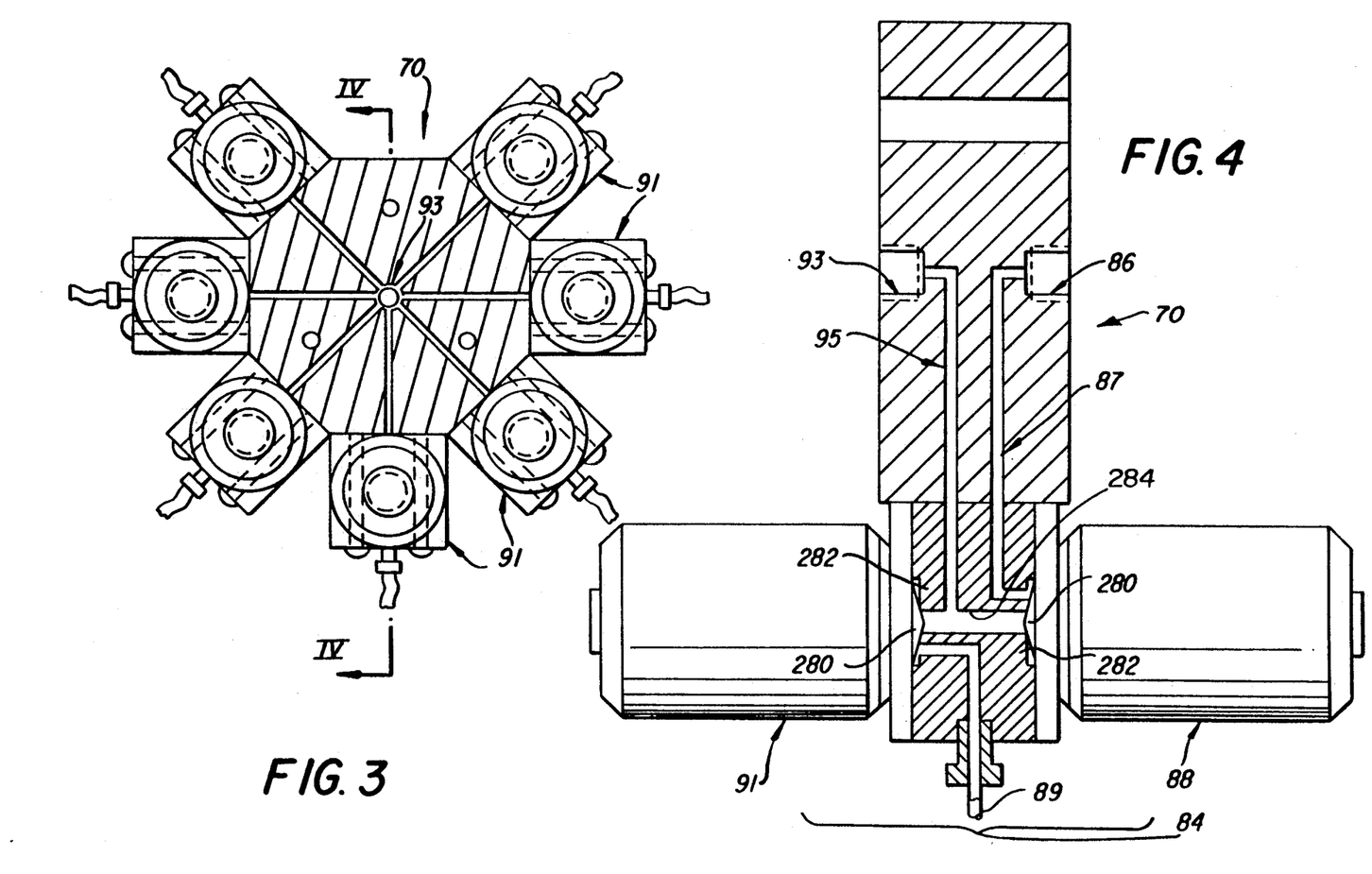
FIG. 3 is section view of the parallel manifold used to supply the base reactants for the synthesizer.
FIG. 4 is a view partially in section, taken generally along the line IV—IV of FIG. 3.

In accord with one aspect of the invention, the arrangement of valves 84 on manifold 70 is as follows:

First, manifold 70 is a parallel manifold, FIGS. 2-4. Incoming line 85, FIG. 2A, enters port 86, to deliver wash liquid acetonitrile as it is supplied from manifold 90, FIG. 2B. From port 86 such liquid passes to each pair of valves 84 via individual channels 87. Each channel 87 feeds to valve portion 88 of each tandem pair 84, FIG. 4. Line 89 supplies a base to a valve portion 91 in each tandem pair 84. Valve portions 88 and 91 include a diaphragm 280 that seats on a valve seat 282, to supply liquid to a common channel 284 that feeds channel 95, if the respective valve portion is open. As is conventional, the diaphragms are solenoid operated, each being independently acting so as to isolate the separate flow paths with minimal dead volume. However, outlet channel 95 carries whatever the output of the two valve portions 88 and 91 provide to it (base or wash liquid).

The two-way valves are preferred over three-way valves for the base manifold 70 in that the dead volume is minimized. Often the base volumes may be less than 100 $\mu l$ delivered in less than a second. Three-way valves tend to displace 100 $\mu l$ when they close, which can upset or alter the delivered volume.

The operation of manifold 70 will be apparent from the above description. First, a valve of a valve pair opens to allow infeed from a bottle, only one at a time, since if two valves were so opened simultaneously, precise flow from each bottle could not be assured. When a particular base is needed in column 110, say for example base A, the corresponding valve portion for that base is opened, valve portion 91 in this case of the pair of valves 84 associated with bottle 72, FIG. 2. When piston 160 is withdrawn as described hereinafter, base A is pushed out of bottle 72 by the constant gas pressure from manifold 62. Base A travels through valve portion 91 into channel 95, common outlet 93, and then line 114. Then an equal volume of activator is allowed to flow by closing valve portion 91 of the valve pair 84 for bottle 72, and opening valve portion 91 of the valve pair 84 for bottle 82. Other bases are added similarly. When the appropriate amount of each base A and activator is passed into the system, including line 95, valve portion 91 is closed and valve portion 88 of the valve pair for bottle 72 is opened, along with the valves of manifold 90 that allow wash liquid, for example $CH_3CN$, to flow into inlet 86. The first step in the wash is to pass the wash liquid through the common channel 284 of valve pair 84 and line 95. The valve portions of pair 84 for bottle 82 are then washed similarly. In this fashion wash liquid is used to push the last bit of each base and activator all the way into column 110. Even some of the wash liquid passes into the column for this purpose. Then the wash side of each valve pair 84 is closed and the wash liquid is directed through each valve 102, 102' and 103 of manifold 90.

Thus, the tandem valve pairs in manifold 90 allow washing, in sequence around the manifold, to insure that all of the base lines (for bases C, G, T, X and Y as well as A) are washed in sequence. This insures that any minor leakage of valve portion 91 of each valve pair 84, is washed away. That is, the invention preferably sequences the washing because each valve orifice may be slightly different, such that an all-at-once wash will not guarantee a wash of leaked base out of each valve portion 91.

This sequence of washing is repeated after each of the bases is passed through column 110.

Figure 5A:
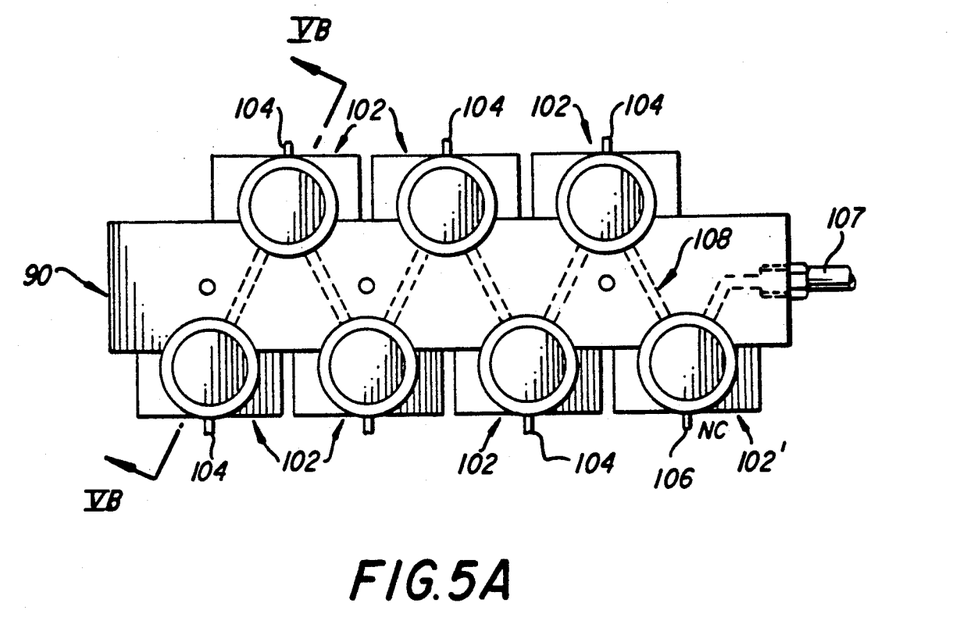
FIG. 5A is a plan view of a series manifold used in the supply of reagents to the synthesizer.
Figure 5B:
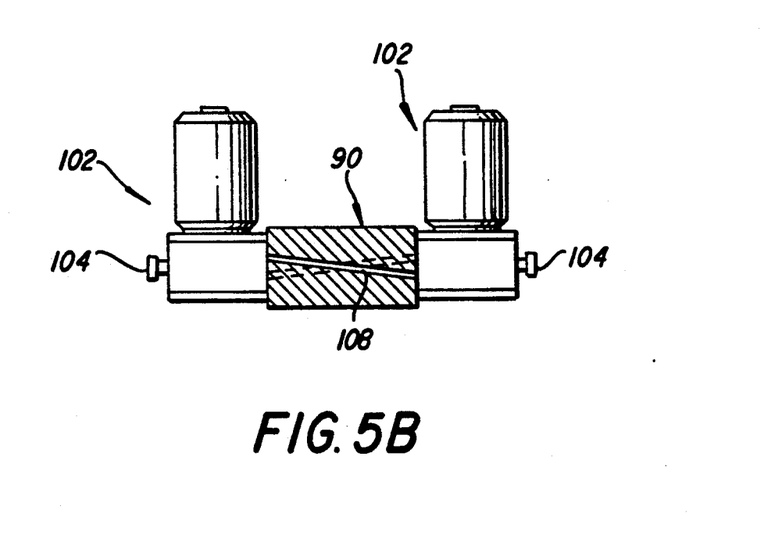
FIG. 5B is a partial section view taken along the line VB—VB of FIG. 5A.

As shown in FIGS. 2, 5A and 5B, manifold 90 is a series manifold, so that each valve 102 or 103 delivers reagent in series as permitted by the positions of each of valves 102. Each valve 102 is preferably a three-way valve and receives liquid from a supply line 104, except for valve 102' that feeds the output of manifold 90 (or manifold 70) via line 106 to column 110 or to line 107 to controlling means 150. Valve 102' receives as its input from a channel 108, FIG. 5A, the liquid supplied through any one of the valves 102.

There is a port 112 in manifold 90, FIG. 2, that is independent of any valve 102, and this is the inlet port for the reactants supplied via line 114 and outlet 93 from manifold 70.

Valves 102, 102' and 103 operate as follows:

In no case is it desirable for more than one valve 102, 102' or 103 to be "open" at any one time, that is, to allow input from the bottle fed by that valve. Pass-through of reagent from another valve 102 is still possible, however. The valve portion "8", FIG. 2, for wash bottle 92 opens on command to feed $CH_3CN$ into manifold 90, when piston 160 is withdrawn. If valve portion "13" is energized, that wash goes to line 85 and manifold 70. When valve portion 13 is deenergized, the wash is shunted on to pass through the porting of all the other valves in manifold 90 that are downstream. To obtain other reagents sequentially, the valve portion associated with that reagent bottle is energized. Valve 102' is of particular importance. It will supply the liquid from valves 102 only either to line 106 or to line 107. Furthermore, flow from manifold 70 is shut off when supplying a reagent from a bottle of manifold 90 by deenergizing valve portion "13".

Preferably, however, as shown and described in FIG. 6, the manifold for the reagent supply means can be a parallel manifold similar to that used for the bases. The reason is that a parallel manifold reduces the system volumes, and contamination of one reagent by another is less likely than in a series manifold. That is, in order to wash manifold 90, the dead volumes of each valve therein must be flushed completely since the next reagent shares the flow volume. The above-noted advantages of two-way valves over three-way valves apply here also. Regarding contamination, any small orifice or leakage at a valve in such a series manifold will contaminate the next (different) reagent that must perforce flow past it.

In FIG. 6, parts similar to those previously described bear the same reference numeral, to which the distinguishing suffix "a" has been appended.

Thus, base manifold 70a receives wash liquid from line 85a and delivers base or wash liquid to valve 102'a, and then to column 110a or controlling means 150a, as described above. Each of the reagents is supplied to its manifold 90a from a respective bottle 92a, 94a, 96a, 98a and 100a, also as described.

Figure 6A:
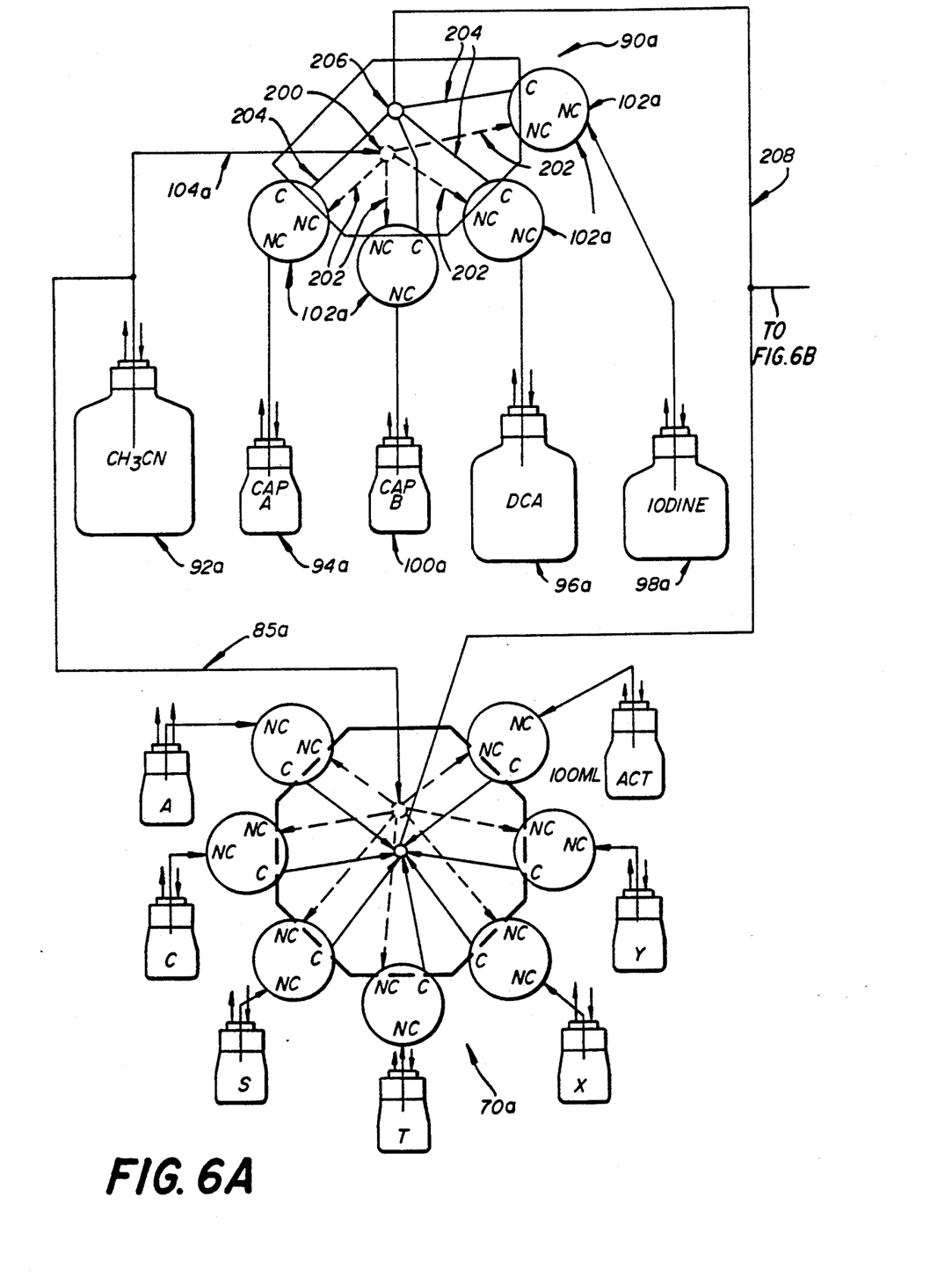

However, manifold 90a. FIG. 6A, is a parallel manifold, and each of the valves 102a is a tandem pair of substantially the same construction as is provided for in valves 84 of FIGS. 2 and 4. Furthermore, no valve is interposed on line 104a between bottle 92a and manifold 90a. Instead, that line feeds wash liquid direct to common inlet 200 for manifold 90a. From there channels 202 carry the wash liquid to each of tandem pair valves 102a. These are constructed identically to the pair shown in FIG. 4, that is, each pair 102a comprises a portion 91 and a portion 88 (not shown in FIG. 6). Each tandem pair valve 102a has an individual outlet channel 204 feeding to a common outlet 206 for manifold 90a, which supplies liquid to line 208 that goes to valve 102'a.

The operation of manifold 90a is readily apparent from the preceding. For example, to detritylate a base in column 110a, FIG. 6B, valve 102'a is energized to connect line 106a to and disconnect line 107a from line 208, and valve portion 91, FIG. 4, of the valve pair 102a for dichloroacetic acid (DCA) is opened. When the piston is withdrawn in controlling means 150a, FIG. 6B, gas pressure pushes DCA into its valve pair 102a and then into common outlet 206, and line 208, FIG. 6A, and eventually into the column. After detritylation, valve portion 91 of valve pair 102a for DCA is closed and portion 88 (FIG. 4) is opened to allow wash liquid from common inlet 200 to wash that valve pair. This wash continues on to column 110a and through it. Thereafter valve 102'a is reversed so that the wash liquid now goes directly to line 107a and controlling means 150a, bypassing column 110a. Valve 102'a is then closed, and a valve 220 (used to combine the functions of valves 154 and 156) is operated to direct the contents of controlling means 150a to waste, as the plunger is advanced. As part of this wash step, wash can be cycled through each of the other valves 102a on the manifold, just as is done on manifold 70a, to be sure to clean up any leaking reagent.

Figure 6B:
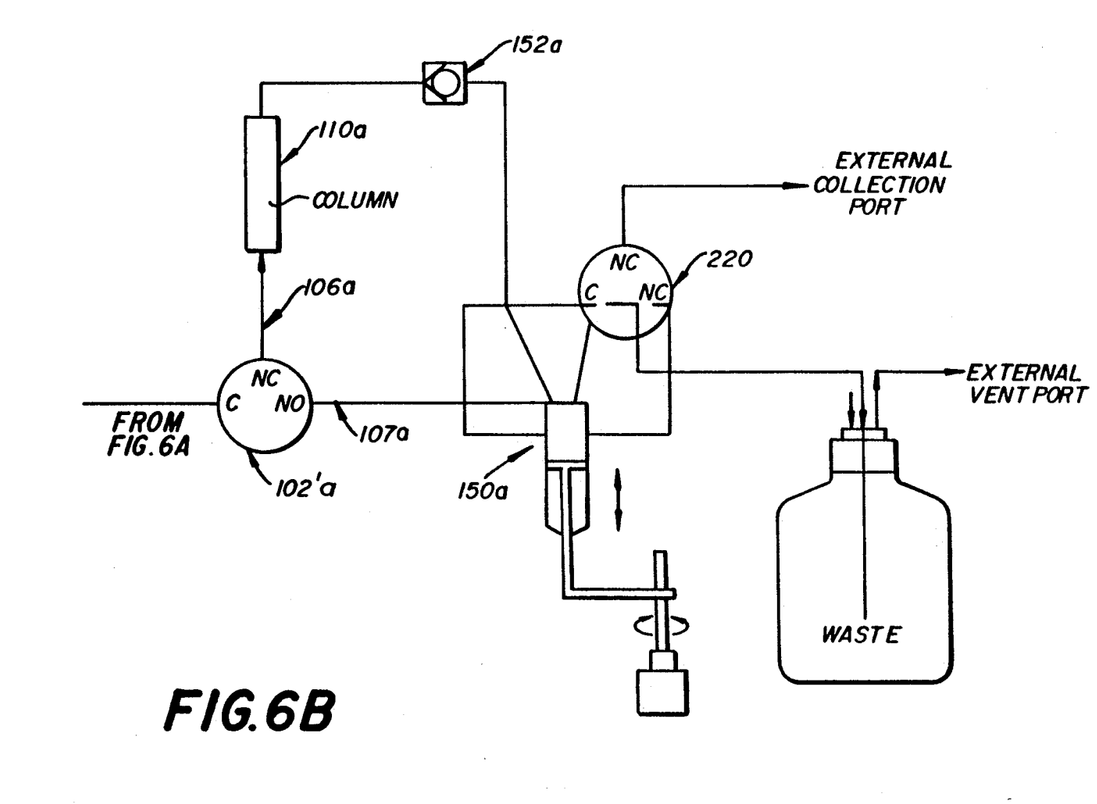

Next, a second base and activator is added, and then the base linkage in column 110a is oxidized, using the iodine of bottle 98a. To this end, valve portion 91 is opened in the valve pair 102 for that bottle, to supply iodine to outlet 206, line 208, valve 102'a and column 110a (as the plunger of controlling means 150a is withdrawn.) Thus, the cycle of reagent/wash, reagent/wash is repeated as was used in the previously described embodiment.

In this embodiment, valve 152 of controlling means 150a has been replaced with a check valve 152a, although as noted below, it too can be eliminated.

Column 110 is a conventional reactor column positioned to receive as input, the output of line 106 from manifold 90 or 70. The finished polynucleotide remains on column 110 for future extraction. Examples of columns that can be used herein include control pore glass types.

In accord with another aspect of the invention, liquid controlling means 150 is positioned fluidly downstream only, from column 110. Means 150 preferably uses a conventional drive or motor means 161, for example, one using a lead screw and a stepper motor. Any conventional low pressure piston and piston chamber can be used. Preferably, however, means 161 include a linear displacement transducer (not shown) to provide direct indication of piston position, so that motor pulse count is not the sole measure of piston movement or position. In a preferred mode of operation, means are also provided that insure that controlling means 150 only receives liquid from, and does not send liquid to, column 110. One mechanism for doing this is the use of two-way valves 152, 154 and 156. Valves 152-156 are conventional two-way valves, and function as follows:

When column 110 is to deliver material via line 120, valve 152 is opened. Otherwise it is preferably closed. Because valve 102' preferably does not connect line 107 with line 106, controlling means 150 is thus prevented from delivering liquid to column 110. Line 107, however, connects directly to controlling means 150, so that when piston 160 is withdrawn, the liquid supplied via manifold 90 enters the chamber 158 when valve 102' is deenergized, assuming a valve to a bottle in either manifold has been opened. Thus controlling means 150 acts to control the supply of all liquid, not just liquid from manifold 70. Because liquid delivered via line 107 is waste material, piston 160 preferably ejects such liquid collected, via valve 156 to waste only.

After piston 160 has emptied any waste in such a fashion, chamber 158 can receive material from column 110 through line 120. Such material includes protecting groups cleaved from the base by an acid environment. To this end, valve 152 is opened. At this point, valve 102' is energized to allow flow from manifold 90 to line 106, but what is supplied to manifold 90 is only the wash liquid $CH_3CN$ from a valve 102. As piston 160 is withdrawn, material is drawn through column 110. Thereafter, valve 152 is closed and valve 154 opened (valve 156 remains closed) and piston 160 is advanced to eject that material from chamber 158 to "collection", where the efficiency of the reaction can be measured as a function of the color density of the cleaved material, as is well-known. For example "collection" can be a fraction collector that separates samples, or such samples can be collected and sent to a spectrophotometer to monitor reaction efficiency. Sampling and monitoring can also be done through a spectrophotometer on line at the external collection port.

Alternatively, valve 152 can be omitted entirely, with the understanding that when piston 160 is advanced to eject liquid from controlling means 150, all valves upstream from column 110 are closed, e.g., valve 102' or all the valves in manifolds 70 and 90. In that case, there is nowhere for liquid in column 110 to flow out, as would be necessary for controlling means to push its liquid back into column 110. Thus, the closing of those upstream valves in a hard liquid flow-path constitutes the means that, in the reacting mode, prevents controlling means 150 from sending liquid from its chamber 158 back into the column.

Preferably a pressure transducer 162 is associated with controlling means 150. The purpose of this transducer is to detect changes in pressure as will occur if a valve operation fails. That is, if a valve fails to energize to allow liquid to feed into a manifold, or is partially blocked, the pressure when piston 160 is withdrawn will drop below a set threshhold valve indicating a system error. If a valve 154 or 156 fails to open when piston 160 advances, pressure will increase beyond a preset value. The synthesizer further preferably includes appropriate circuitry 163 for comparing the signal generated by transducer 162, with the preset safety levels. When the signal from transducer 162 varies beyond the present level by a predetermined amount, the circuitry shuts down the synthesizer and issues an error code, allowing for real time diagnostics.

The following is a representative example illustrating the steps of operation using synthesizer 60. These steps are synchronized by computing means (not shown), which can be any conventional programmed computer system, using for example one or more microprocessors.

Column 110 is provided with a support having a tritylated base already on it. Thus, the first step in the process is to detritylate that base. This is accomplished by opening only valve 102' to the column and a reagent valve portion "11" of a valve 102, so that when piston 160 is withdrawn, the extra volume that is created allows the gas pressure from manifold 62 to push DCA into valve 102' and line 106, and then into the column. Following the requisite amount of DCA being drawn into the system, valve portion "11" is closed and valve portion "8" of valve 102 is opened, to allow enough wash liquid into manifold 90 and column 110 to push all the DCA through that is needed. This also serves to wash out valve 102' and line 106 of any DCA, prior to using the next reagent. The detritylate waste is also drawn into chamber 158 from column 110. Valve 102' is then closed, valve 154 or 156 is opened, and piston 160 is advanced. This causes chamber 158 to empty into the waste line or to the collection line where the trityl groups can be collected and analyzed.

Next, a new base is added, along with ACT in a predetermined ratio. This is done as follows:

Line 114 already has wash liquid in it, so that the energizing of valve 102' with all the valves 102 of manifold 90 being closed, and the opening of a valve portion 91 of tandem valves 84 will cause one of the bases and then ACT to be drawn sequentially into outlet 93 of manifold 70, and then on into column 110. (Valve 102' is energized to pass liquid to line 106 of the column rather than to syringe 158.) When the appropriate amount of that base and ACT has been drawn into line 114 and column 110 (by the operation of piston 160), the respective valve portion 91 in manifold 70 or 70a is closed and the wash portion 88 for that particular tandem pair is opened to allow $CH_3CN$ to pass into that valve pair, line 95 and outlet 93. After enough wash liquid has been drawn to clear line 114 and line 106 of that base (and then of ACT) into column 110, each of the other wash valves around manifold 70 are opened sequentially (with valve 102' operated to divert flow directly into chamber 158), as described above. This causes the other base lines 95 to be washed of any possible leaking bases, which wash is sent via chamber 158 and valve 156 to waste.

Thereafter, the linkage between the two bases in column 110 is oxidized, using the iodine reagent. The process is essentially identical to that described above for DCA, except that valve portion "12" of the valves 102, associated with the iodine, controls its flow. Washing occurs after this, using the process described for DCA wherein $CH_3CN$ is used to push all the iodine through the column.

Next, capping of the base in column 110 is achieved by allowing flow of both cap A and cap B reagents in a predetermined ratio into manifold 90. This is done by energizing valve portions 9 and 10, respectively, for those reagents and valve 102' to allow flow from manifold 90 to column 110, when piston 160 of chamber 158 is withdrawn. Each cap reagent is completely drawn into the column by following it with wash liquid $CH_3CN$, that also washes the valves 102 corresponding with the cap reagents.

Alternatively, after each of the reagents has been drawn into manifold 90 and column 110, the wash valve 8 is energized to wash all of the valves 102 even though only one such valve has been used for the particular reagent.

It will be appreciated that after each of the above reagents and wash has flowed into column 110 and chamber 158, the chamber is emptied into the waste line by opening valve 156.

The process is then repeated for each of the other bases from bottles 72, 74, 76, 78, 79 and 80, as needed for the particular polynucleotide sequence.

Figure 7:
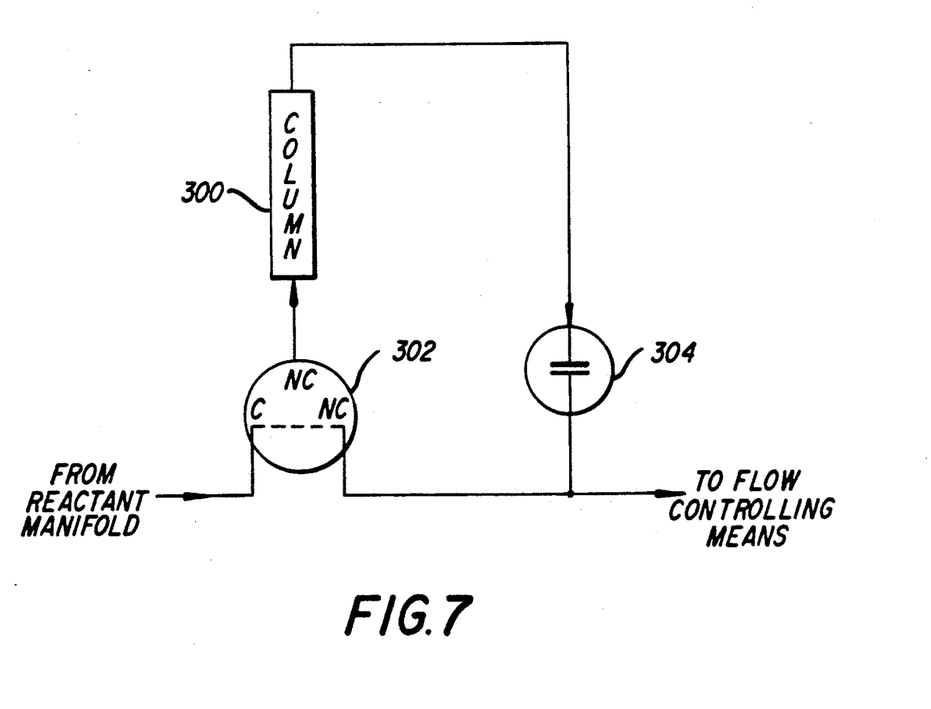
FIG. 7 is a fragmentary schematic illustration similar to FIG. 2, illustrating an alternative embodiment.

Alternatively, FIG. 7, dual or multiple columns 300 mounted in parallel, can be used. If two columns are present, the second one can be mounted to receive reactant from the parallel manifold via a valve 302 in the reagent manifold, which then feeds via a normally closed valve 304 to a second controlling means not shown, as described for the first column. Such multiple columns can be used with accurate flow rates and volumes, even if both columns are producing two different sequences simultaneously.

The invention has been described in detail with particular reference to preferred embodiments thereof, but it will be understood that variations and modifications can be effected within the spirit and scope of the invention.

What is claimed is:

1. In a synthesizer apparatus for synthesizing peptides or polynucleotides, the apparatus including supply means for supplying a) liquid reactants for synthesizing the peptides or polynucleotides, b) liquid reagents that assist in said synthesis, and c) a wash liquid; a first reactor column; means for fluidly connecting said supply means with said first reactor column; means for positively displacing with gas pressure, liquid reactants and reagents, and wash liquid from said supply means into said connecting means; and controlling means connected to said first reactor column and containing a temporary storage chamber, for allowing liquid to flow under the force of said gas pressure and at a controlled rate, into said temporary storage chamber and for thereafter emptying the temporary storage chamber;

the improvement wherein said apparatus further includes means for delivering liquid from said first reactor column to said controlling means and wherein said controlling means is a positive displacement controlling means that contacts said delivered liquid and is fluidly positioned only downstream of said first reactor column, and further including means for preventing flow from said temporary storage chamber back to said first reactor column, so that said first reactor column is precluded from contamination by reactants or reagents in said controlling means, and said controlling means needs no cleaning to prevent it from contaminating said first reactor column, and wherein said apparatus further includes a parallel manifold having i) sufficient inlet means to receive each of said liquid reactants, ii) a common inlet to receive the wash liquid, and iii) an outlet connected to said connecting means to supply reactant or reagent to said first reactor column or said controlling means, each of said inlet means including a pair of tandem two-way valves, both of the valves of said pair having a common outlet that feeds into said manifold outlet, one portion of each pair of said tandem valves being connected to said common inlet for said wash liquid and the other portion of said valves being connected to said inlet means for one of said liquid reactants, and means for selectively opening only one of the pairs of tandem valves at a time to a source of wash liquid, in a predetermined sequence, whereby an adequate source of wash liquid can be provided for each of said valve pairs of said parallel manifold.

2. Apparatus as defined in claim 1, wherein said controlling means include a piston and cylinder, and means for driving said piston.

3. Apparatus as defined in claim 2, wherein said controlling means include means for providing direct indication of piston position.

4. Apparatus as defined in claim 1, and further including means in said controlling means for detecting pressure changes, and further including comparator means for comparing the pressure detected by said detecting means with a preset safety level, whereby the improper performance of a valve can be detected.

5. Apparatus as defined in claim 1, wherein said pairs of tandem valves comprise solenoid valves.

6. Apparatus as defined in claim 1, and further including an additional reactor column connected in parallel with said first reactor column, to a controlling means.

* * * * *